United States Patent
Durand et al.

(10) Patent No.: US 8,173,843 B2
(45) Date of Patent: May 8, 2012

(54) AMPHIPHILIC DERIVATIVES OF α-C-PHENYL-N-TERT-BUTYLNITRONE

(75) Inventors: Grégory Durand, Villeneuve les Avignon Cedex (FR); Ange Polidori, Avignon (FR); Bernard Pucci, Molleges (FR); Jean-Pierre Salles, Eguilles (FR)

(73) Assignees: TS Pharma, Eguilles (FR); Universite d'Avignon Et des Pays du Vaucluse, Avignon Cedex (FR)

( * ) Notice: Subject to any disclaimer, the term of this patent is extended or adjusted under 35 U.S.C. 154(b) by 580 days.

(21) Appl. No.: 12/282,755

(22) PCT Filed: Mar. 15, 2007

(86) PCT No.: PCT/FR2007/000446
§ 371 (c)(1),
(2), (4) Date: Feb. 17, 2009

(87) PCT Pub. No.: WO2007/118974
PCT Pub. Date: Oct. 25, 2007

(65) Prior Publication Data
US 2009/0306001 A1    Dec. 10, 2009

(30) Foreign Application Priority Data
Mar. 17, 2006    (FR) ...................................... 06 02355

(51) Int. Cl.
*C07C 291/02*    (2006.01)
*A61K 31/13*    (2006.01)
*A61K 31/7034*    (2006.01)

(52) U.S. Cl. .................. 564/299; 514/644; 536/17.9
(58) Field of Classification Search .................. 564/299; 514/644; 536/17.9
See application file for complete search history.

(56) References Cited

U.S. PATENT DOCUMENTS
7,655,251 B2 *    2/2010    Durand et al. ................. 424/401

FOREIGN PATENT DOCUMENTS
WO    WO 99/20601    4/1999
WO    WO 2004/043982    5/2004

OTHER PUBLICATIONS

Durand et al. J. Med. Chem., 2003, 46, p. 5230-5237.*
International Search Report and Written Opinion for PCT/FR2007/000446 filed Mar. 15, 2007.
Ouari O et al.: "Synthesis of a Glucolipidic Amphiphilic Nitrone as a New Spin Trap"; Journal of Organic Chemistry, American Chemical Society, Easton, US; vol. 64, 1999; pp. 3554-3556; XP002250820.

* cited by examiner

*Primary Examiner* — Shaojia Anna Jiang
*Assistant Examiner* — Jonathan S Lau
(74) *Attorney, Agent, or Firm* — Alston & Bird LLP

(57) ABSTRACT

Compounds derived from α-C-phenyl-N-tert-butylnitrone, a process for the preparation thereof and use thereof for the preparation of medicaments for use in preventing or treating oxidative stress-related diseases.

10 Claims, 4 Drawing Sheets

US 8,173,843 B2

AMPHIPHILIC DERIVATIVES OF α-C-PHENYL-N-TERT-BUTYLNITRONE

CROSS REFERENCE TO RELATED APPLICATIONS

This application is a national stage application filed under 35 U.S.C. 371 of International Application No. PCT/FR2007/0004446, filed Mar. 15, 2007, which claims priority from French patent application 06 02355, filed Mar. 17, 2006.

FIELD AND BACKGROUND OF THE INVENTION

The invention relates to novel compounds derived from α-C-phenyl-N-tert-butylnitrone, to a process for the preparation thereof and to the use thereof for the preparation of medicaments for use in preventing or treating oxidative stress-related diseases.

Pathologies related to oxidative stress and to the formation of oxygen free radical species have been listed by Croos C. E., *Arch. Intern. Med.* (1987) 107, 526-545 and by Anderson K. M., Ellis G., Bonomi P., Harris J. E., *Medical Hypotheses* (1999) 52, 53-57.

There are many of them: more than 70 pathologies of this type are mentioned in this list, which includes in particular immune and inflammatory diseases, ischemia-reperfusion syndrome, atherosclerosis, Alzheimer's disease, Parkinson's disease, lesions due to UV radiation and ionizing radiation, certain forms of chemical carcinogenesis and also cell aging.

Oxygen free-radical species and nitrogen free-radical species (ROSs and RNSs) are produced naturally in the organism and the regulation thereof is ensured by certain specialized enzymes such as soluble superoxide dismutase (SODs). The trapping of these extremely reactive free-radical species is essential since they bring about irreversible damage in the cell. While the normal production of these free-radical species is easily regulated by the cell, an overproduction of free radicals related to an external oxidative stress (inflammatory shock, ischemia-reperfusion syndrome, etc.) or a genetic defect (mitochondrial anomalies in particular) leads to rapid cell degradation. It then becomes impossible for the human or animal organism to deal with this large flux of radicals.

There are several defense mechanisms against oxidative stress of the cell, which are capable of operating at various levels of the oxidative cascade. This cascade is generally initiated by the overproduction of superoxide radicals related to a partial reduction in molecular oxygen in the mitochondrion (typical ischemia-reperfusion syndrome). This superoxide radical can undergo dismutation to hydrogen peroxide. These two species, by means of the Fenton reaction, in the presence of ferrous iron, can give hydroxyl radicals which have the particularity of reacting very rapidly and nonspecifically with any of the cell components, such as lipids, DNA or proteins, causing irreversible damage among them, as has been described by Stadtman H. R., Berlett B. S. *J. Biol. Chem.* (1991) 266, 17201-17211; Floyd R. A. *Carcinogenesis* (1990) 11, 1447-1450; Gille J. J., Van Berkel C. G., Joenge H. *Carcinogenesis* (1994) 15, 2695-2699; Halliwell B. *Mutat. Res.* (1999) 443, 37-52. These free-radical species, by activating certain suicide genes (Bcl or p53 genes) through the NF-κB factor, are also responsible for the phenomenon of cell apoptosis which has been described by Siebenlist U., Franzoso G., Brown K., *Annu. Rev. Cell. Biol.* (1994) 10, 405-455.

Soluble SOD is responsible for converting the superoxide radical to hydrogen peroxide, the latter subsequently being processed by glutathione-dependent peroxidases or catalases.

Other cellular levels of protection against oxidizing agents exist, in particular at the membrane level, which make it possible to limit the oxidation of unsaturated membrane phospholipids. α-Tocopherol and β-carotene are the main examples of lipid antioxidants.

The most promising strategy in the search for a therapy for use in preventing or treating oxidative stress-related diseases consists in intervening as far upstream as possible in this oxidative cascade, in order to prevent, very early on, the damage related to the very high reactivity of the free-radical species.

For this, it has been sought to trap these highly reactive free radicals by means of "spin trap" molecules, among which nitrones appear to be the most effective.

The therapeutic effect of nitrones in the reduction and prevention of damage caused by free radicals in biological systems was demonstrated in 1990 by Oliver C., Starke-Read P., Stadman E., Liu G., Carney J., Floyd R. *Proc. Natl. Acad. Sci. USA* (1990) 87, 5144-5147.

These authors were able to demonstrate a decrease in the damage caused by cerebral ischemia after injection of α-C-phenyl-N-tert-butylnitrone (PBN) in gerbils. The cerebral ischemia is accompanied by a large increase in the production of free radicals which were trapped by the PBN so as to form spin adducts which are much more stable and therefore much less reactive and toxic. PBN is the spin trap which has been the subject of the most biological studies.

Reference may, for example, be made to Hensley K., Carney J. M., Stewart C. A., Tabatabaie T., Pye Q. N., Floyd R. A. *Int. Rev. Neurobiol.* (1997) 40, 229-317.

PBN has a high specificity of action in the brain, probably due to its high hydrophobicity, which allows it to cross the blood-brain barrier, as has been shown by Cheng H. Y., Liu T., Feuerstein G., Barone F. C. *Free Radic. Biol. Med.* (1993) 14, 243-250.

Among the nitrones, the most well known and the most effective are α-C-phenyl-N-tert-butylnitrone (PBN), 5,5-dimethylpyrrolidine-N-oxide (DMPO) and molecules discovered more recently: N-benzylidene-1-diethoxyphosphoryl-1-methylethylamine N-oxide (PBNP) and 5-diethylphosphono-5-methylpyrroline-N-oxide (DEPMPO).

Mention may also be made of a disulfonate derivative of PBN, NXY-059 (disodium 4-[(tert-butylimino]methyl-benzene-1,3-disulfonate N-oxide), which has a neuroprotective activity greater than PBN and which is undergoing pharmacological study and clinical development:

Kuroda S., Tsuchidate R., Smith M. L., Maples K. R., Siesjo B. K. *J. Cereb. Blood Flow Metab.* (1999) 19, 778-787; Lees K. R., Sharma A. K., Barer D., Ford G. A., Kostulas V., Cheng Y. F., Odegren T. *Stroke* (2001) 32, 675-680.

However, none of the molecules mentioned above has a satisfactory efficacy in vivo or ex vivo at low dose, even if their cytotoxic concentration is very high: Almli L. M., Hamrick S. E. G., Koshy A. A., Täuber M. G., Ferriero D. M. *Dev. Brain Res.* (2001) 132, 121-129; Nakao N., Grasbon-Frodl E. M., Widner H., Brundin P. *Neuroscience* (1996) 73, 185-200. This lack of efficacy is probably related to poor bioavailability of the drug and to a problem of cell penetration.

There remains therefore the need for a molecule of spin trap type, capable of trapping free radicals, and which is also capable of being conveyed by the human or animal organism to its target at the intracellular level;

In particular, a molecule capable of crossing the cell membrane and, an even greater and more difficult challenge, the mitochondrial membrane in order to enter into the compartment where the superoxide radical is produced.

With this aim, Ouari O., Polidori A., Pucci B., Tordo P., Chalier F. *J. Org. Chem.* (1999) 64, 3554-3556 and Geromel V., Kadhom N., Cebalos-Picot I., Ouari O., Polidori A., Munnich A., Rötig A., Rustin P. *Hum. Mol. Genet.* (2001) 10, 1221-1228 have proposed a perfluorocarbon-based amphiphilic derivative of PBN: TA1PBN.

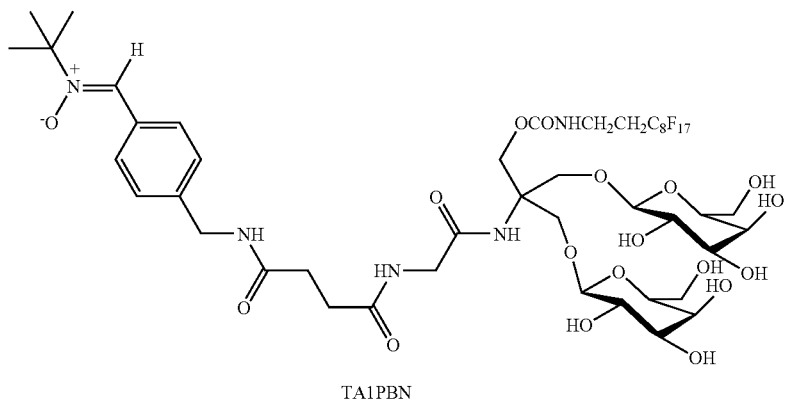

TA1PBN

This molecule has been tested on cell lines of fibroblasts suffering from a severe respiratory chain complex V (ATPase) deficiency and has given encouraging results.

However, the synthesis of TA1PBN presents difficulties which render its production on the industrial scale difficult to envision.

International application WO 2004/04982 describes α-C-phenyl-N-tert-butylnitrone derivatives. These spin-trap-type molecules are easy to synthesize and capable of trapping free radicals and they have good bioavailability. One of these compounds, N-[4-(octa-O-acetyllactobionamidomethylene) benzylidene]-N-[1,1-dimethyl-2-(N-octanoyl)amido]ethylamine N-oxide, or LPBNAH, has shown a biological activity greater than that of PBN in oxidative aging tests (B. Poeggeler et al., Journal of Neurochemistry, 2005, 95, 962-973). However, there remains the need for compounds having an even greater activity, and with further increased bioavailability.

The applicant set itself the objective of designing and producing novel molecules, having a spin-trap activity, exhibiting an increased bioavailability compared with the prior art molecules, and the preparation of which is simple and makes it possible to envision production on the industrial scale.

SUMMARY OF THE INVENTION

A subject of the invention is novel molecules, characterized in that they correspond to formula (I) below:

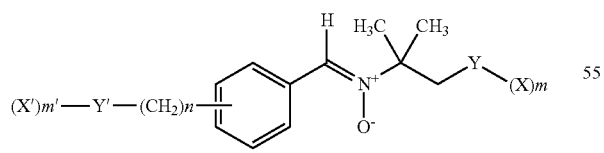

(I)

in which:

X represents a hydrophilic group chosen from a monosaccharide or a polysaccharide, and also the aminated derivatives of monosaccharides and of polysaccharides, a polyethylene oxide chain, a peptide chain, and an ionic polar group chosen from a quaternary ammonium, an amine oxide, a carnitine group, a phosphate group, a choline group, a group

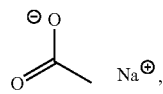

and a group

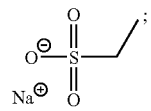

m represents an integer equal to 1, 2 or 3;

Y represents a spacer arm or a bond intended to link the hydrophilic substituents X to the rest of the molecule;

Y is chosen from ester, amide, urea, urethane, ether, thioether and amine functions and $C_1$-$C_6$ hydrocarbon-based chains, optionally interrupted with one or more ester, amide, urea or urethane functions and with one or more ether, amine or thioether bridges;

Y' represents a group chosen from: an ester function

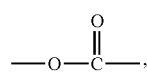

an amide function

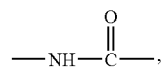

a urea function

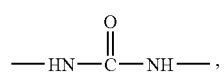

a urethane function

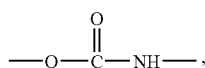

an ether bridge —O—, a thioether bridge —S—; one or more amino acids and serinol;
n is an integer equal to 0, 1 or 2;
m' represents an integer equal to 1 or 2;
X' represents a hydrogen atom or a $C_4$-$C_{14}$ alkyl chain optionally substituted with one or more fluorine atoms.

The substituent $(X')_{m'}$—Y—$(CH_2)_n$—, placed on the aromatic ring, may be in the ortho-, meta- or para-position.

Among the monosaccharides that can be used in the present invention, mention may be made of: glucose, lactose, fructose, mannose, galactose, ribose, maltose and sucrose. Mention may also be made of open-chain monosaccharides. Among the amino sugar derivatives, mention may in particular be made of glucosamine and galactosamine. Among the polysaccharides that can be used in the present invention, mention may be made of chains consisting of several monosaccharide units, for instance: sucrose, maltose and lactobionic acid.

When the hydrophilic part X of the molecule of formula (I) is a polyethylene oxide chain, the latter advantageously comprises from 30 to 100 ethylene oxide units, preferably from 50 to 60 units.

Preferably, the peptide chain consists of natural amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine.

Examples of ionic or nonionic hydrophilic groups that can be used in the present invention are given in scheme 1 below.

Scheme 1: General structure of the polar heads

Ionic polar heads

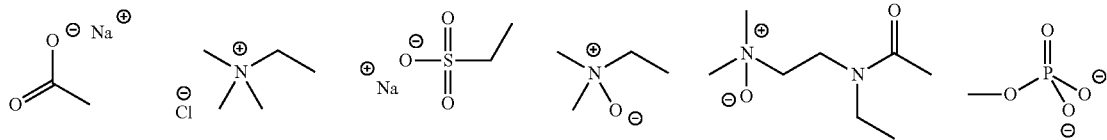

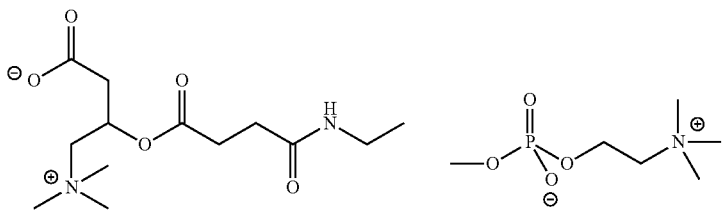

Nonionic polar heads

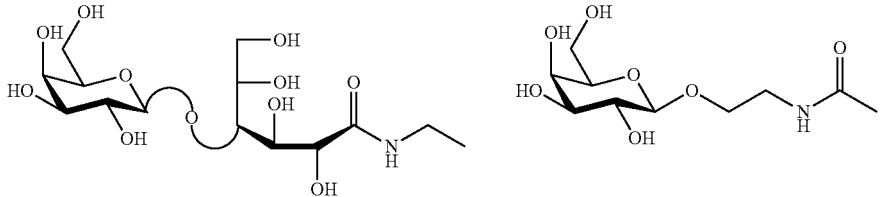

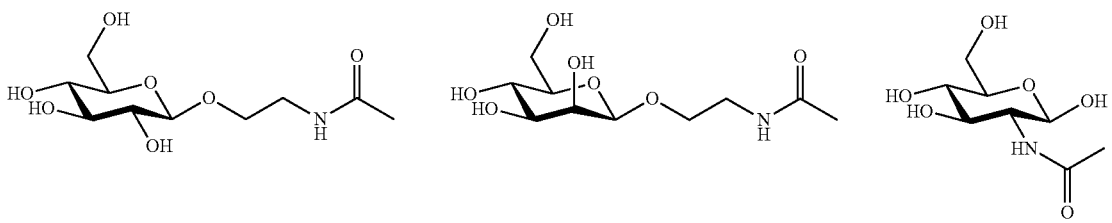

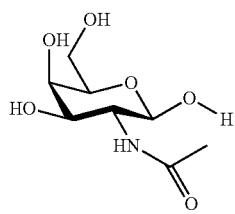
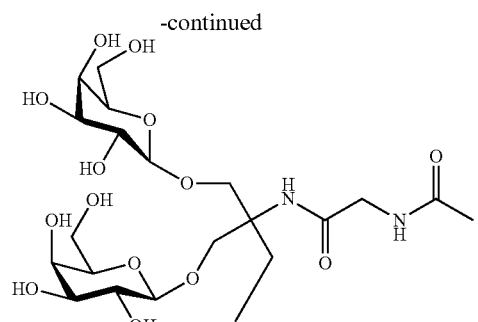
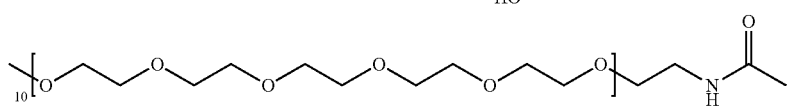
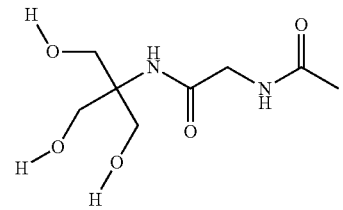

Depending on whether the spacer arm Y is monofunctional or plurifunctional, it is substituted once or twice with the group X.

The group X' may, for example, be chosen from the following radicals:

octyl radical;

hydrocarbon-based radicals: n-butyl, tert-butyl, isobutyl, n-pentyl, isopentyl, n-hexyl, n-heptyl, n-octyl, n-nonyl, n-decyl, n-undecyl, n-dodecyl, n-tridecyl, n-tetradecyl, etc.;

fluorinated hydrocarbon-based radicals: mention may be made of those corresponding to the formula —$(CH_2)_r$—$(CF_2)_tF$, in which r and t represent two integers with: $14 \geq r+t \geq 4$, such as, for example: —$(CF_2)_4F$; —$(CF_2)_5F$; —$(CF_2)_6F$; —$(CF_2)_7F$; —$(CF_2)_8F$; —$(CF_2)_9F$; —$(CF_2)_{10}F$; —$(CF_2)_{11}F$; —$(CF_2)_{12}F$; —$(CF_2)_{13}F$; —$(CF_2)_{14}F$; —$CH_2$—$(CF_2)_3F$; —$CH_2$—$(CF_2)_4F$; —$CH_2$—$(CF_2)_5F$; —$CH_2$—$(CF_2)_6F$; —$CH_2$—$(CF_2)_7F$; —$CH_2$—$(CF_2)_8F$; —$CH_2$—$(CF_2)_9F$; —$CH_2$—$(CF_2)_{10}F$; —$CH_2$—$(CF_2)_{11}F$; —$CH_2$—$(CF_2)_{12}F$; —$CH_2$—$(CF_2)_{13}F$; —$(CH_2)_2$—$(CF_2)_2F$; —$(CH_2)_2$—$(CF_2)_3F$; —$(CH_2)_2$—$(CF_2)_4F$; —$(CH_2)_2$—$(CF_2)_5F$; —$(CH_2)_2$—$(CF_2)_6F$; —$(CH_2)_2$—$(CF_2)_7F$; —$(CH_2)_2$—$(CF_2)_8F$; —$(CH_2)_2$—$(CF_2)_9F$; —$(CH_2)_2$—$(CF_2)_{10}F$; —$(CH_2)_2$—$(CF_2)_{11}F$; —$(CH_2)_2$—$(CF_2)_{12}F$; —$(CH_2)_3$—$(CF_2)_1F$; . . . —$(CH_2)_{13}$—$(CF_2)F$.

Preferably, at least one of the requirements below is met:
X represents a lactobionamide or carnitine group or a polyoxyethylene chain;
m represents 1;
m' represents 1 or 2;
n represents 1;
X' is chosen from the radicals octyl, heptyl, octyl, decyl, dodecyl and $CF_3(CF_2)_rCH_2CH_2$— with $8 \geq r \geq 6$.

A subject of the invention is also a process for preparing the compounds corresponding to formula (I), this process being characterized in that an aldehyde corresponding to formula (II) is reacted with a hydroxylamine corresponding to formula (III) according to scheme 2 below:

Scheme 2

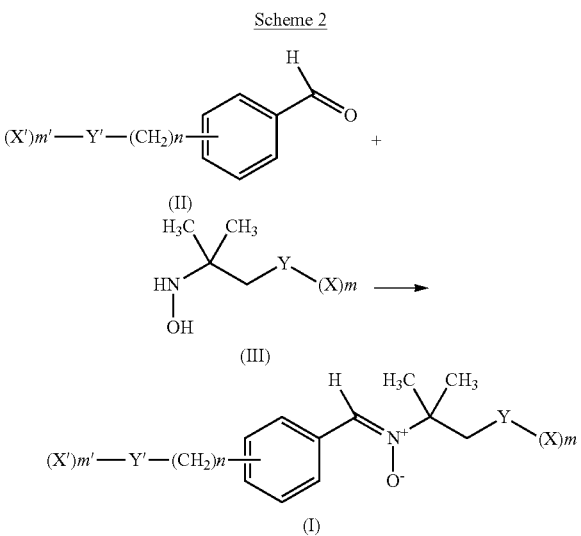

in which X, m, Y, X', m', n and Y' have the same definition as above.

The compounds of formula (III) are prepared according to a process described in scheme 3 below:

Scheme 3

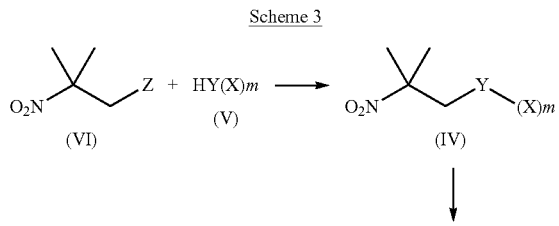

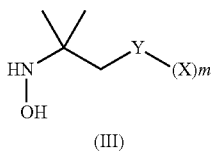

(III)

Z = OH, NH₂ or Tosyl

Depending on the monocatenary or bicatenary nature of the lipophilic group, scheme 2 is carried out under conditions which will be disclosed below. By way of example, a common lactobionamide polar head was chosen.

DETAILED DESCRIPTION a—Synthesis of the Lactobionamide Hydrophilic Part

Figure 1:
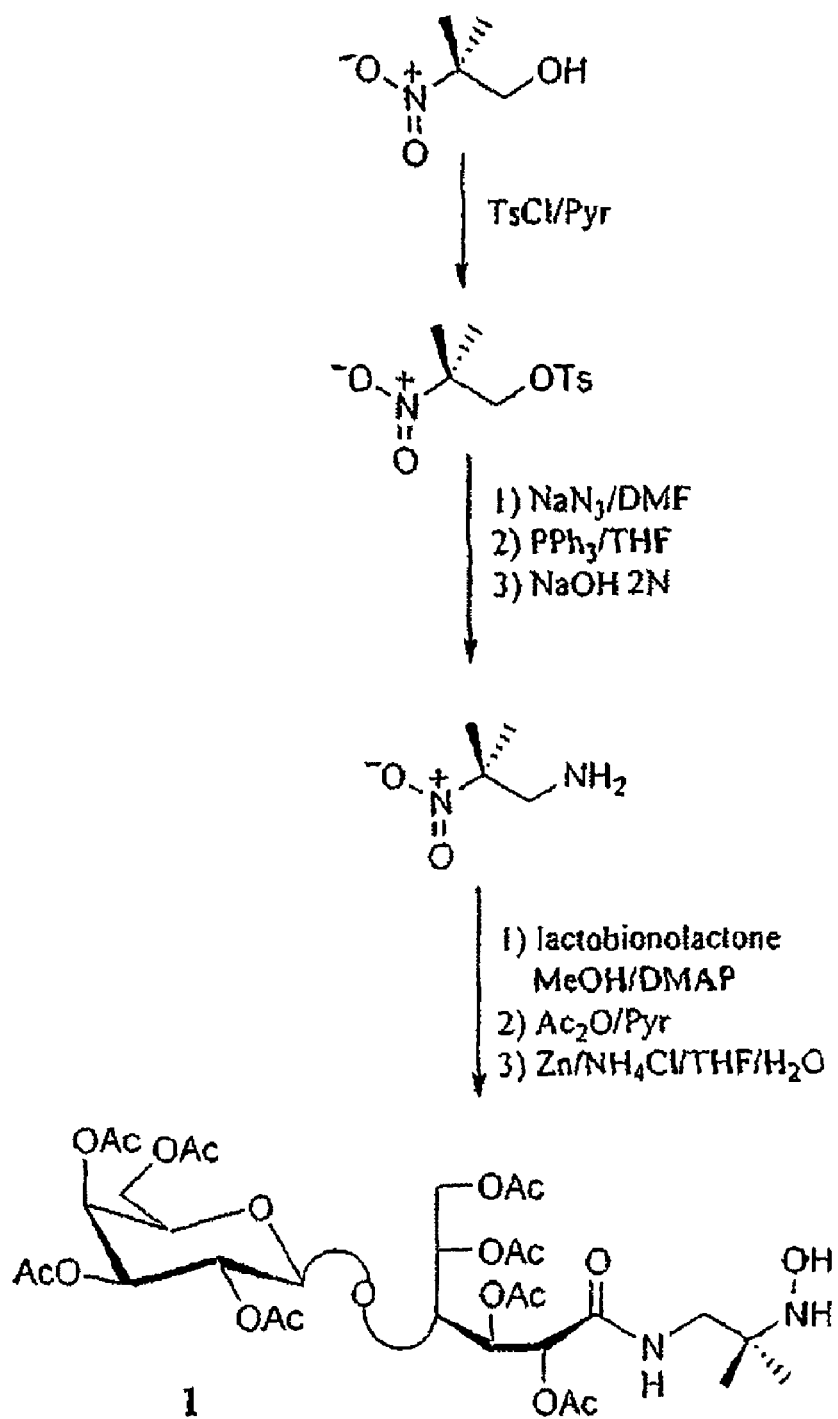
FIG. 1 illustrates the preparation of the compound of formula (III)

FIG. 1 illustrates the preparation of the compound of formula (III) with:
m=1;
X=lactobionamide;

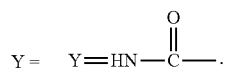

The hydrophilic part is synthesized from 2-methyl-2-nitropropanol.

The alcohol function is converted to amine by tosylation followed by substitution with sodium azide. The alkyl azide is converted, by means of a Staudinger reaction, to amine in the presence of triphenylphosphine and sodium hydroxide.

This amine can react with lactobionolactone; this reaction makes it possible to graft the polar head via an amide bond.

The nitro function is subsequently reduced to hydroxylamine by means of 4 equivalents of zinc in a THF-water mixture in the presence of ammonium chloride.

Figure 2:
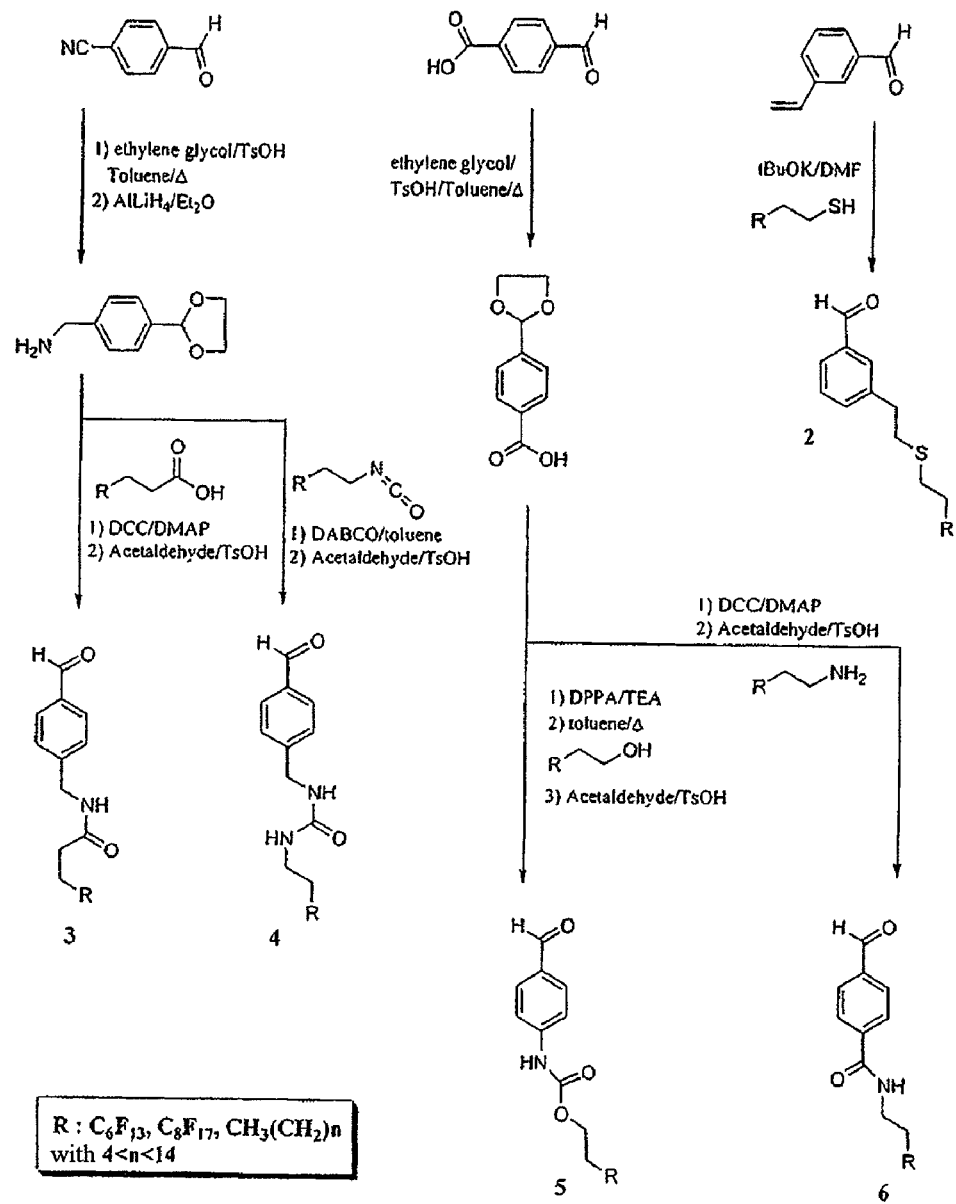
FIG. 2 illustrates the preparation of the compounds of formula (II)

The reduction reaction makes it possible to obtain compound 1 with an 80% yield.

b—Synthesis of The Hydrocarbon-Based or Perfluoro-Carbon-Based Monocatenary Hydrophobic Part (FIG. 2):

FIG. 2 illustrates the preparation of the compounds of formula (II) comprising an aliphatic chain with:
n=0, 1 or 2;
X'=(CH₂)₂—R with R=C₆F₁₃, C₈F₁₇ or CH₃(CH₂)ₙ; 4<n<14;

(compound 2)

(compound 3)

(compound 4)

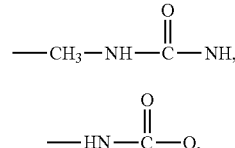

(compound 5)

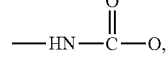

(compound 6)

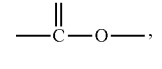

(compound 7)

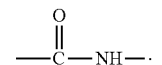

Figure 3:
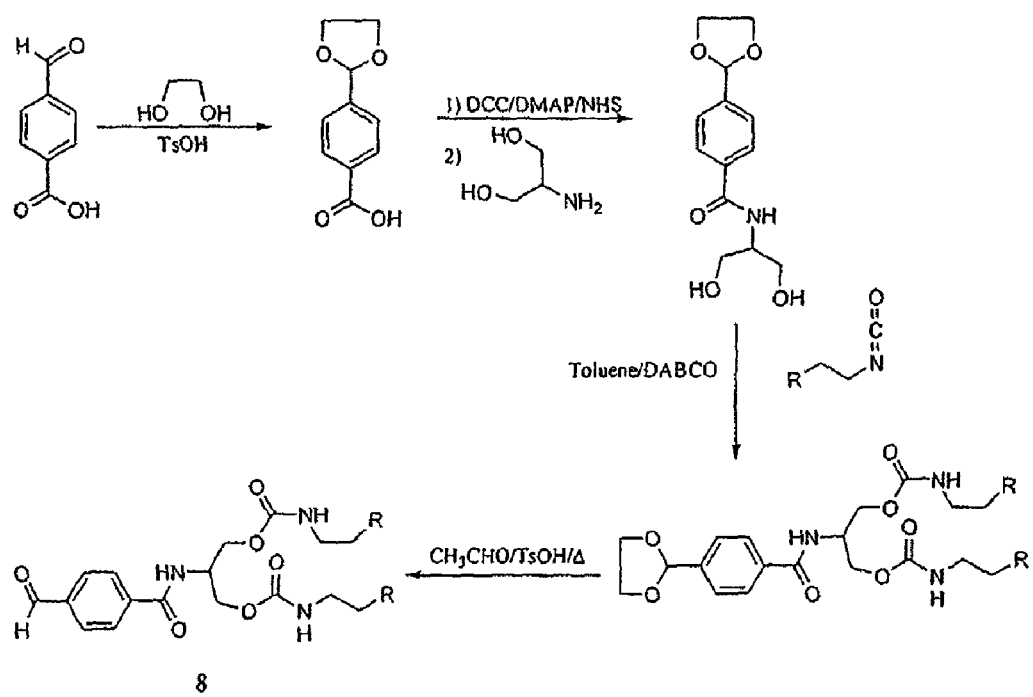
FIG. 3 illustrates the synthesis of the bicatenary hydrophobic part from serinol.

Derivative 2 is obtained from 3-vinylbenzaldehyde by direct condensation, in a basic medium, of the aliphatic thiol. Compound 3 is synthesized from 4-cyanobenzaldehyde. The aldehyde function is protected by acetalization and the nitrile function is reduced to an amine function. The acid function of the aliphatic chain is condensed thereon. The product 4 is obtained by condensation of the isocyanate of the aliphatic chain on this amine in toluene. The aldehyde function of these two compounds is deprotected by transacetalization in acetaldehyde. Derivatives 5, 6 and 7 are synthesized from 4-carboxybenzaldehyde, the aldehyde function of which is protected beforehand by acetalization. Compound 5 is obtained after having obtained the acyl azide by treatment with diphenylphosphorylazide. The azide is transposed to isocyanate by heating in toluene. The aliphatic alcohol is condensed in the presence of DABCO so as to obtain compound 5 after transacetalization. Compound 6 is obtained from the acid by coupling, in the presence of a peptide coupling agent, dicyclohexylcarbodiimide, of the aliphatic amine and deprotection of the aldehyde by heating in an acidic medium in acetaldehyde.

c—Synthesis of The Hydrocarbon-Based or Perfluoro-Carbon-Based Bicatenary Hydrophobic Part (FIG. 3):

FIG. 3 illustrates the synthesis of the bicatenary hydrophobic part from serinol.

Figure 4:
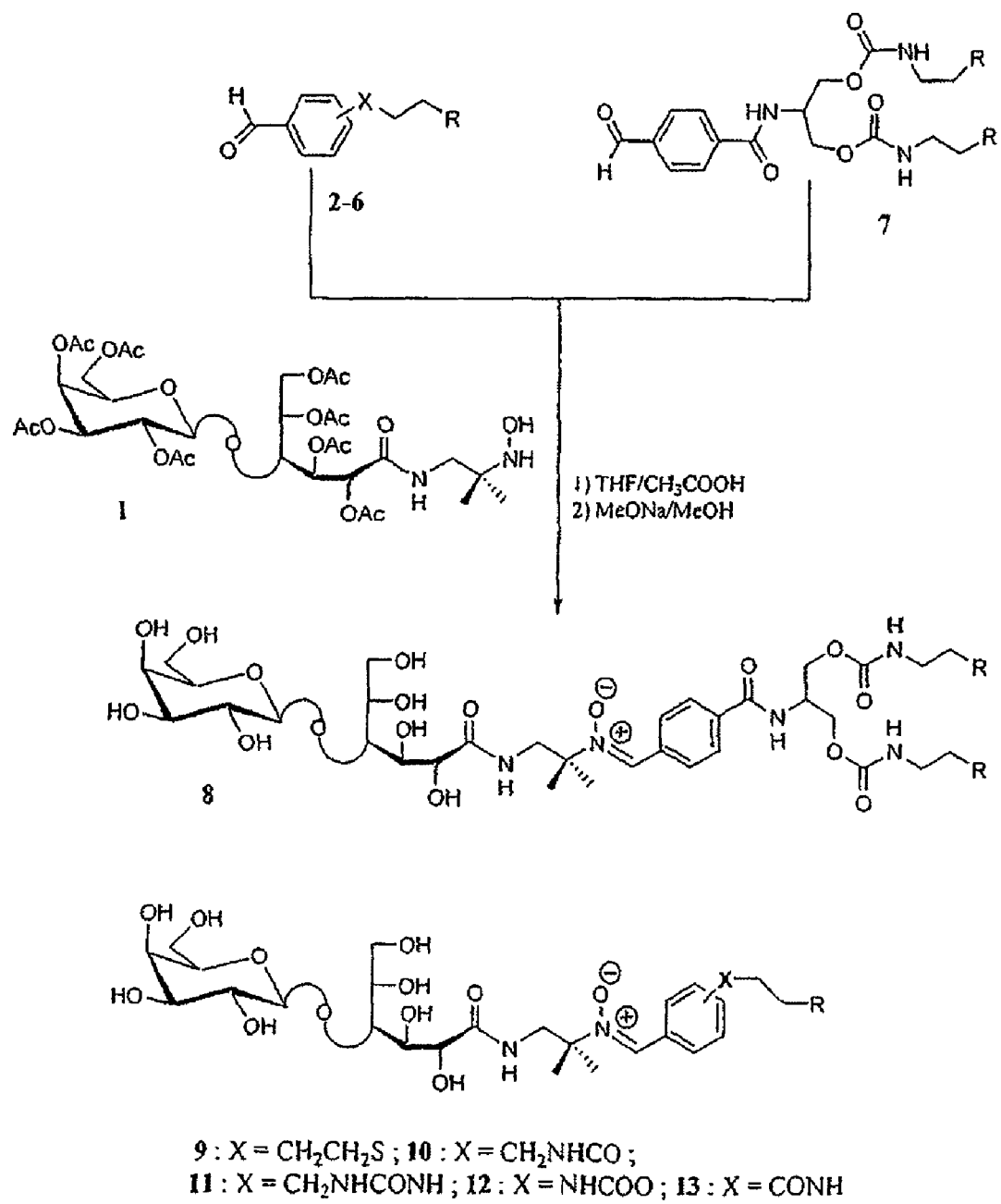
FIG. 4 illustrates the production of lactobionolactone-derived monocatenary and bicatenary amphiphilic nitrones.

Compound 7 is obtained from 4-carboxybenzaldehyde. The aldehyde function is protected by acetalization. The serinol is condensed on the acid function after the latter has been activated by coupling of N-hydroxysuccinimide in the presence of dicyclohexylcarbodiimide. The aliphatic chains are condensed on the alcohol functions by condensation of alkyl isocyanates in toluene. Compound 8 is obtained after transacetalization in acetaldehyde.

d—Production of Lactobionolactone-Derived Mono-Catenary and Bicatenary Amphiphilic Nitrones (FIG. 4):

The various amphiphilic nitrones are produced by coupling of the aldehyde function of the various hydrophobic synthons on the hydroxylamine group of the lactobionamide hydrophilic part. The coupling reaction is carried out under argon in a THF/acetic acid mixture for 24 h.

All the nitrones were purified by reverse-phase HPLC (C18 column/methanol-water eluent).

A subject of the invention is also the use of the compounds corresponding to formula (I) as defined above, as a free-radical scavenger.

In fact, it has been demonstrated that the compounds according to the present invention have a capacity for trapping free radicals which is equivalent to that of the prior art compounds.

This property makes it possible to envision the use of the molecules of the invention in varied fields:

in the therapeutic field, the products of the invention may be used in the prevention and/or treatment of pathologies related to oxidative stress and to the formation of free-radical oxygen species.

A subject of the invention is consequently the pharmaceutical compositions comprising a compound according to the invention in a pharmaceutically acceptable carrier. A subject of the invention is the use of a compound according to the invention for the preparation of a medicament for use in preventing and/or treating the effects of free radicals.

A subject of the invention is also the use of a compound of the invention for the preparation of a pharmaceutical composition for use in preventing and/or treating pathologies related to oxidative stress and to the formation of free-radical oxygen species, in particular immune and inflammatory diseases, ischemia-reperfusion syndrome, atherosclerosis, Alzheimer's disease, Parkinson's disease, Huntington's disease, lesions due to UV radiation and ionizing radiation, cancers and cell aging.

The products of the invention can be administered by any route known to those skilled in the art, in particular by intravenous or intramuscular injection, or by oral or cutaneous administration. They may be used alone or in combination with other active agents. The dosage thereof and the amount administered daily are adjusted according to the activity measured for the molecule in question and according to the weight of the patient;

in the cosmetics field, the compounds of the invention may be used for preventing and/or treating the effects of aging and also the effects of solar radiation.

A subject of the invention is therefore also a cosmetic composition comprising a compound of the invention in a cosmetically acceptable carrier.

Said composition may be for application to the skin or to the appendages, (nails, hair).

It may be in the form of an aqueous or oily solution, a water-in-oil or oil-in-water emulsion, a triple emulsion or an ointment.

The compounds of the invention may be introduced into any cosmetic composition for which a free-radical-scavenging activity is desired: a skincare cream, an antisun product, a makeup-removing product, a mask for the skin or the hair, a shampoo, a makeup product such as a lipstick, a face powder, a foundation, a nail varnish, etc.;

in the organic synthesis field, the compounds of the invention can be used as agents for taking up free radicals in free-radical reactions.

Due to their solubility in varied media, the compounds of the invention are easy to use and can be employed under very diverse conditions.

EXPERIMENTAL SECTION

I—Biological Evaluation

The biological tests were carried out according to the procedures described in Journal of Neurochemistry, 2005, 95, 962-973. In order to evaluate the potentialities of these novel derivatives, we measured the ability of compound 10 to reduce and prevent apoptotic cell death phenomena. Hydrogen peroxide is very widely used as an apoptosis inducer in many cell models. Thus, the viability of Sprague-Dawley rat embryo cortex cell cultures is greatly impaired after treatment with hydrogen peroxide at concentrations of 50 to 200 μM. The addition of PBN (10 μM) makes it possible to very incompletely restore the viability of these cultures. The addition of compound 10 at the same concentration (10 μM) makes it possible, on the other hand, to completely restore the viability of such cultures, thus demonstrating an effectiveness in reducing oxido-induced apoptosis phenomena 5 to 10 times greater than that of PBN. These same cultures were also subjected to a mitochondria-selective oxidative stress inducer, doxorubicin (Kotamraju S.; Konorev E. A.; Joseph J.; Kalyanaraman B. *J. Biol. Chem.* 2000, 275, 33 585-33 592). The observations are the same as for the induction with hydrogen peroxide. While PBN produces only a partial protection against cell death, compound 10 allows the cell viability to be completely maintained. These preliminary results underline the great ability of compound 10 to prevent apoptosis phenomena induced at varying cell levels. It can reduce the intracellular damage caused by treatment with hydrogen peroxide, but its effectiveness with respect to doxorubicin also suggests an increased incorporation of this derivative into the mitochondrial compartment. A dysfunction of the mitochondrion, the central organelle in the control of apoptosis is involved in a very wide variety of pathological conditions. The anti-apoptotic properties of derivative 10 combined with its incorporation into the mitochondrion make it possible to envision its use in the fields mentioned above.

II—Example

Synthesis of the Lactobionamide Monocatenary Nitrone 10 (R=$C_5H_{11}$)

1—Synthesis of Compound 1

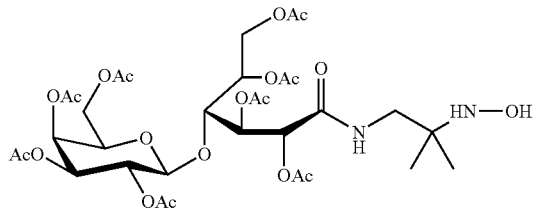

Compound 1 precursor of the polar head can be readily prepared from 2-methyl-2-nitropropanol according to a method already described in WO 2004/043982: the 2-methyl-2-nitropropanol is converted to 2-methyl-2-nitropropylamine by means of a series of 3 steps consisting: 1—in activating the alcohol function, forming a sulfonic ester of tosyl chloride, 2—in substituting this sulfonyl ester with an azido group, 3—in selectively reducing the azido group to an amine by means of the Staudinger reaction. The 2-methyl-2-nitropropylamine is condensed with lactobionolactone in methoxyethanol in a basic medium at 60° C. This reaction is followed by a reaction of peracetylation of the hydroxyl groups in an acetic anhydride/pyridine mixture. Finally, the nitro group is selectively reduced to a hydroxylamine according to a procedure widely described in the literature (Janzen E. G.; Dudley R. L.; Shetty R. V. *J. Am. Chem. Soc.* 1979, 101, 243-245). The reaction is carried out in a THF/$H_2O$ mixture at ambient temperature in the presence of powdered zinc and ammonium chloride. Compound 1 is then easily purified by silica gel chromatography (eluent: EtOAc/cyclohexane, 8:2, v/v) to give a white powder with a yield of 25% from the 2-methyl-2-nitropropanol.

$R_f$=0.52 (eluent: EtOAc/MeOH, 9:1, v/v)

$^1$H NMR (CDCl$_3$) δ (ppm): 6.62 (1H); 5.58-5.63 (2H); 5.39 (1H); 5.03-5.25 (3H); 4.68 (1H); 4.55 (2H); 4.35 (1H); 3.95-4.21 (3H); 3.27 (2H); 1.99-2.18 (24H); 1.06 (6H).

$^{13}$C NMR (DMSO) δ (ppm): 166.7-170.7 (CO); 101.1 (CH); 78.4, 72.1, 70.8, 70.2, 70.0, 69.5, 69.3, 69.3, 67.6 (CH); 61.7, 61.4, 57.4 (CH$_2$); 45.4 (C); 22.8, 20.9 (CH$_3$).

2—Synthesis of Compound 3

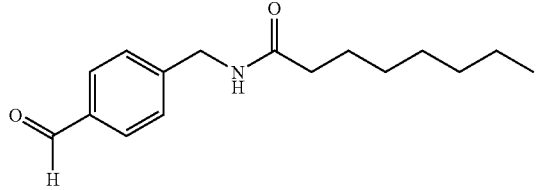

Compound 3 bearing the hydrocarbon-based chain can be readily prepared from 4-cyanobenzaldehyde according to a method already described in WO 2004/043982: the 4-cyanobenzaldehyde is converted to 4-(1,3-dioxacyclopent-2-yl) benzylamine by means of a series of 2 steps consisting: 1—in protecting the aldehyde function in the form of dioxolane, 2—in reducing the cyano group to an amine.

The 4-(1,3-dioxacyclopent-2-yl)benzylamine is condensed with octanoic acid in dichloromethane in the presence of a peptide coupling system consisting of DCC and HOBt according to a method already described (Ouari O.; Polidori A.; Pucci B.; Tordo P.: Chalier F. *J. Org. Chem.* 1999, 64, 3554-3556) and then the dioxolane protecting group is removed by treatment in a 1:1, v/v, acetic acid/water mixture. Compound 3 is subsequently purified by silica gel chromatography (eluent: cyclohexane/EtOAc, 6:4, v/v) to give a white powder with a yield of 40% from the 4-cyanobenzaldehyde.

R$_f$=0.47 (eluent: EtOAc/cyclohexane, 6/4 v/v)

$^1$H NMR (CDCl$_3$) δ (ppm): 9.98 (1H); 7.84 (2H); 7.42 (2H); 6.18 (1H); 4.50 (2H); 2.26 (2H); 1.63 (2H); 1.29 (8H); 0.88 (3H).

$^{13}$C NMR (CDCl$_3$) δ (ppm): 191.9, 173.0 (CO); 137.0, 139.7 (C); 127.9, 126.8 (CH); 65.3, 43.3, 36.8, 31.7, 29.3, 29.0, 25.8, 22.6 (CH$_2$); 14.1 (CH$_3$).

3—Synthesis of Compound 1$\overline{0}$

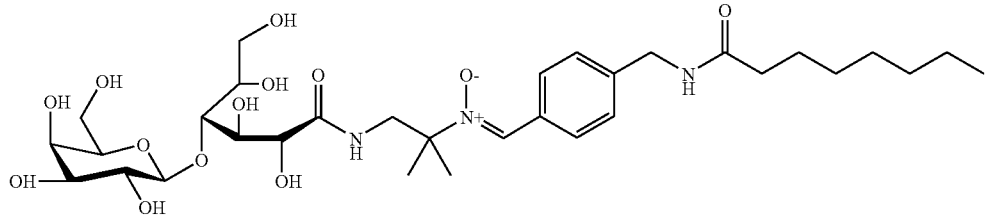

Compound 10 is obtained by condensation of compound 1 with compound 3 according to a method already described in WO 2004/043982: the hydroxylamine 1 and the benzaldehyde derivative 3 are solubilized in stoichiometric amount in anhydrous THF under an argon atmosphere and in the presence of molecular sieve 4A. The reaction medium is brought to 60° C. in the dark. The hydroxylamine is added sequentially every 24 hours in fractions of 0.20 equivalent until the benzaldehyde derivative is used up. The use of acetic acid as cosolvent makes it possible to considerably increase the reaction kinetics, as has already been demonstrated (Poeggeler B.; Durand G.; Polidori A.; Pappola M. A.; Vega-Naredo L.; Conto-Montes A.; Böker J.; Hardeland R.; Pucci B. *J. Neurochem.* 2005, 95, 962-973). The nitrone formed is purified by silica gel chromatography (eluent: EtOAc/cyclohexane, 7:3 v/v) and then by size exclusion chromatography on Sephadex LH-20 resin (eluent: dichloromethane/methanol, 1:1 v/v). Finally, the acetyl groups of the polar head are eliminated according to the Zemplen method by transesterification in methanol in the presence of a catalytic amount of sodium methanolate. Compound 10 is purified by size exclusion chromatography on Sephadex LH-20 resin (eluent: methanol) to give a white powder with a yield of 70%.

Rf=0.38 (eluent: EtOAc/MeOH/H$_2$O, 7:2:1, v/v).

$^1$H NMR (MeOD) δ (ppm): 8.35 (2H); 7.89 (1H); 7.41 (2H); 4.30-4.71 (3H); 4.19 (1H); 3.32-3.90 (13H); 2.28 (2H); 1.61 (8H); 1.33 (8H); 0.93 (3H).

$^{13}$C NMR (MeOD) δ (ppm): 174.2 (CONH); 142.4, 135.1 (C); 129.2, 129.9, 127.1, 104.3, 81.7, $\overline{75}$.8, 73.3 (CH); 72.5 (C); 71.7, 71.3, 71.1, 68.9 (CH); 62.3, 61.3, 45.7, 42.4, 35.7, 31.5, 28.9, 28.7, 25.7 (CH$_2$); 23.5, 23.4 (CH$_3$); 22.3 (CH$_2$); 13.0 (CH$_3$).

The invention claimed is:

1. A compound, characterized in that it corresponds to formula (I):

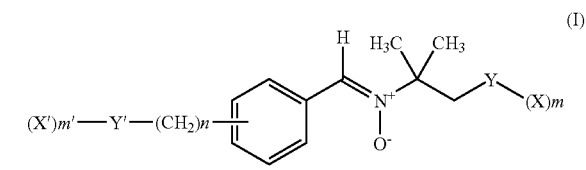

in which:

X represents a hydrophilic group chosen from a monosaccharide or a polysaccharide, and also the aminated derivatives of monosaccharides and of polysaccharides, a polyethylene oxide chain, a peptide chain, and an ionic polar group chosen from a quaternary ammonium, an amine oxide, a carnitine group, a phosphate group, a choline group, a group

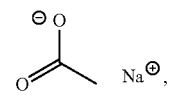

and a group

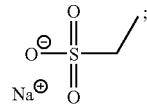

m represents an integer equal to 1, 2 or 3;
Y represents a spacer arm or a chemical bond intended to link the aromatic ring and the hydrophilic substituents X;
Y is chosen from a chemical bond or an ester, amide, urea, urethane, ether, thioether and amine functions and C1-C6 alkyl chains optionally interrupted with one or more ester, amide, urea or urethane functions and with one or more ether, amine or thioether bridges;
Y' represents a group chosen from: an ester function, an amide function, an urea function, an urethane function, an ether bridge, a thioether bridge, one or more amino acids and serinol;
m' represents an integer equal to 1 or 2;
n is equal to 0, 1 or 2;
X' represents a hydrogen atom or a C4-C14 alkyl chain optionally substituted with one or more fluorine atoms.

2. The compound as claimed in claim 1, characterized in that X represents a group chosen from: glucose, lactose, fructose, mannose, galactose, ribose, maltose, glucosamine, sucrose and lactobionamide.

3. The compound as claimed in claim 1, characterized in that X represents a group chosen from polyethylene oxide chains comprising from 30 to 100 ethylene oxide units, preferably from 50 to 60 units.

4. Compound according to claim 1, characterized in that X represents a group chosen from any one of the following:

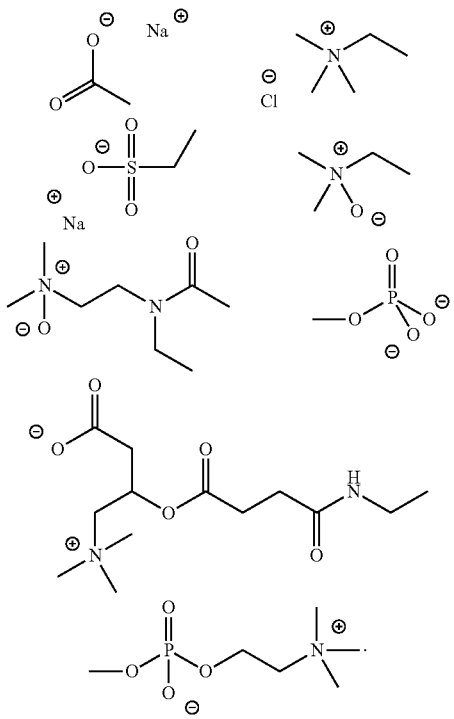

5. The compound as claimed in claim 1, characterized in that at least one of the requirements below is met:
X represents a group chosen from: lactobionamide, carnitine or a polyoxyethylene chain;
m represents 1;
m' represents 1 or 2;

n is equal to 1;
X' is chosen from octyl, decyl, dodecyl and CF3(CF2)rCH2CH2-;
$8 \geq r \geq 6$.

6. A process for preparing a compound corresponding to formula (I) as claimed in claim 1, this process being characterized in that an aldehyde corresponding to formula (II) is reacted with a hydroxylamine corresponding to formula (III) according to scheme 2 below:

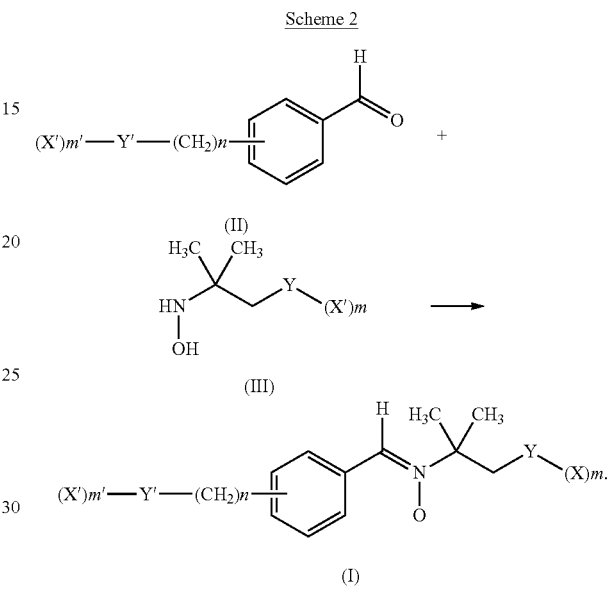

7. The process as claimed in claim 6, characterized in that the compound of formula (III) is prepared according to a process described in scheme 3:

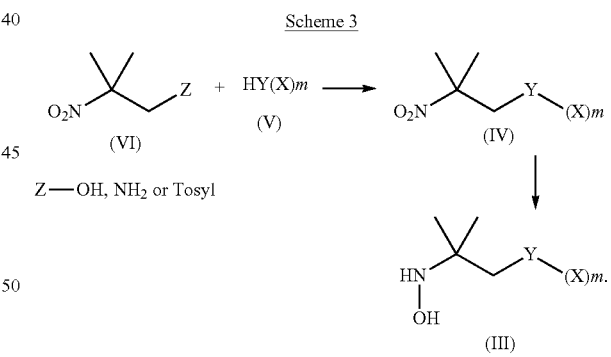

8. A pharmaceutical composition comprising at least one compound corresponding to formula (I) as claimed in claim 1, in a pharmaceutically acceptable carrier.

9. A cosmetic composition, characterized in that it comprises at least one compound corresponding to formula (I) as claimed in claim 1, in a cosmetically acceptable carrier.

10. A method of organic synthesis comprising taking up free radicals in free-radical reactions with the compound corresponding to formula (I) as claimed in claim 1.

* * * * *